United States Patent [19]
Fujii et al.

[11] Patent Number: 5,277,871
[45] Date of Patent: Jan. 11, 1994

[54] LIQUID CHROMATOGRAPHIC ANALYZER, SAMPLE FEEDER AND PRELABELING REACTION TREATING METHOD

[75] Inventors: Yoshio Fujii, Katsuta; Kasumi Yoshida, Mito; Junkichi Miura, Katsuta; Hiroshi Satake, Katsuta; Masahito Ito, Katsuta, all of Japan

[73] Assignee: Hitachi, Ltd., Tokyo, Japan

[21] Appl. No.: 5,310

[22] Filed: Jan. 19, 1993

Related U.S. Application Data

[63] Continuation of Ser. No. 596,537, Oct. 12, 1990, abandoned.

[30] Foreign Application Priority Data

Oct. 20, 1989 [JP] Japan .................................. 1-271667

[51] Int. Cl.⁵ ............................................. B01D 15/08
[52] U.S. Cl. ...................................... 422/70; 422/68.1; 422/63; 422/65; 422/100; 436/161; 436/179; 436/180; 210/656
[58] Field of Search ............... 422/70, 68.1, 82.07, 422/82.08, 63, 65, 100; 436/161, 172, 174, 49, 54, 179, 180; 210/656

[56] References Cited

U.S. PATENT DOCUMENTS

| | | | |
|---|---|---|---|
| 4,070,284 | 1/1978 | Fujita et al. | 422/70 X |
| 4,314,823 | 2/1982 | Rich, Jr. et al. | 422/70 X |
| 4,456,037 | 6/1984 | Gocho | 422/64 X |
| 4,837,707 | 5/1909 | Amano et al. | 364/497 |
| 4,849,110 | 7/1989 | Takata et al. | 436/161 X |
| 4,969,993 | 11/1990 | Nash, Jr. et al. | 210/198.2 |
| 4,980,130 | 12/1990 | Metzger et al. | 422/70 X |
| 5,011,608 | 4/1991 | Damjanovic | 436/161 |

Primary Examiner—James C. Housel
Assistant Examiner—Long V. Le
Attorney, Agent, or Firm—Antonelli, Terry, Stout & Kraus

[57] ABSTRACT

The present invention provides a liquid chromatographic analyzer for analyzing a sample containing components for analysis by reacting the sample with a pre-labeling reagent to obtain a reaction mixture containing labeled components, concentrating the reaction mixture and separating the labeled components from each other, and detecting the separated labeled components by a detector, the steps of analysis being controlled to concurrently proceed by a control unit, thereby shortening the time for analysis per sample which analyzer includes: (a) a unit for storing samples containing components for analysis and a pre-labeling reagent for the components at a constant temperature, (b) a unit for reacting the sample with the pre-labeling reagent at a constant temperature to obtain a reaction mixture containing labeled components, (c) a unit for transferring one of the samples and the pre-labeling reagent from unit (a) to unit (b), (d) a unit for concentrating the reaction mixture and separating the labeled components from each other, (e) a unit for detecting the separated labeled components, and (f) a unit for controlling the steps of analysis to concurrently proceed, thereby shortening the time for analysis per sample.

13 Claims, 8 Drawing Sheets

FIG. 3A

| STEP | OPERATION | NUMBER OF CYCLES AND PASSAGE OF TIME (MIN) | | |
|---|---|---|---|---|
| | | n | n + 1 | n + 2 |
| | | 0      5 | 10 | 15 |
| 1 | CLEANING OF REACTION VESSEL | — | — | --- |
| | CHARGING OF SAMPLE | — | — | -- |
| | CLEANING OF NOZZLE | - | - | - |
| | CHARGING AND MIXING OF REAGENT | — | — | --- |
| | REACTION | —— | —— | ----- |
| 2 | INTRODUCTION OF SAMPLE INTO METERING TUBE | - | - | - |
| | CONCENTRATION | — | — | — |
| | TRANSFER OF SAMPLE | — | — | — |
| | REGENERATION OF PRE-COLUMN | — | — | — |
| 3 | SEPARATION | ------ | —— | —— |
| | DETERMINATION | ------ | —— | —— |
| | DATA DISPLAY AND OUTPUT | --- | — | — |

FIG. 3B

| SAMPLE INTRODUCING VALVE 47 | METERING | a | a | a |
| | TRANSFERRING | b | b | b |
| COLUMN CHANGE-OVER VALVE 52 | CONNECTING | c | c | c |
| | SYNCHRONOUS TREATING | d | d | d |

| STEP | OPERATIONS | NUMBER OF CYCLES AND PASSAGE OF TIME (MIN) | | |
|---|---|---|---|---|
| | | n | n+1 | n+2 |
| | | 0          5          10          15 | | |
| 1 | CLEANING OF REACTION VESSEL | — | — | -- |
| | CHARGING OF SAMPLE | — | — | -- |
| | CLEANING OF NOZZLE | — | — | -- |
| | CHARGING AND MIXING OF REAGENT | — | — | --- |
| | CHARGING OF SAMPLE | — | — | -- |
| 2 | REACTION | — | — | — |
| | REGENERATION OF PRE-COLUMN | — | — | — |
| | INTRODUCTION OF SAMPLE INTO METERING TUBE | — | — | — |
| | CONCENTRATION | — | — | — |
| 3 | TRANSFER OF SAMPLE | --- | — | — |
| | SEPARATION | ----- | ----- | ----- |
| | DETERMINATION | ----- | ----- | ----- |
| | DATA DISPLAY AND OUTPUT | -- | — | — |

LIQUID CHROMATOGRAPHIC ANALYZER, SAMPLE FEEDER AND PRELABELING REACTION TREATING METHOD

This application is a continuation application of application Ser. No. 596,537, filed Oct. 12, 1990, now abandoned.

BACKGROUND OF THE INVENTION

This invention relates to an analyzer making use of the principle of liquid chromatography and a method of treating the samples for the analyzer. More particularly, the invention relates to a method and an apparatus suited for labeling a sample before separating its components.

Liquid chromatography is characterized by its capability to selectively analyze a specific component after separating the components of a substance in the state of a solution. It is appliable to the analyses of many important items in the field of clinical examinations. On the other hand, liquid chromatography necessitates complicate means of analysis and takes much time for the analysis in many cases. This has been a bar for applying a liquid chromatography to the routine works in chemical or medical checkups such as clinical examinations where a large number of specimens must be treated within a limited period of time. This demerit has been responsible for the delay of spread of the automatic apparatus for this type of analysis.

Analysis of catecholamines can be named as one of the items of analysis which are backward in adaptation to routine works. It is admitted to be a useful item for diagnostic examinations of cellular tumors, abnormalities in circulatory organs, cerebral nervous system, endocrinal metabolism, etc., stress and other morbid states. Therefore, the analysis of catecholamines is attracting attention as a useful and diagnostically important item for group examination of geriatric diseases.

Liquid chromatographic separation and analysis of catecholeamines is generally carried out by reacting the sample with a fluorescent labeling agent and subjecting the reaction product to determination by a fluorophotometer. As for the labeling techniques, there are known two types of method: pre-labeling method in which the sample is reacted with the labeling agent before separating the components by a separating column and post-labeling method in which the reaction with the labeling agent is performed after separating the components by a separating column. The post-labeling method is incapable of high-sensitivity detection because of wide diffusion of components after elusion through the separating column. So that the pre-labeling method is advantageous for determining a trace component in a vital specimen.

As the prior art for labeling (turning into a derivative) catecholamines by the pre-labeling method and subjecting the labeled catecholamines to chromatographic analysis, there are known the methods disclosed in JP-A-61-88148 and 60-143766.

According to the method of JP-A-61-88148, alumina is added to the sample to have catecholamines adsorbed on the alumina while reacting dansyl chloride therewith in the course of adsorption to turn said catecholamines into the derivatives. Then, the derivatives are desorbed from the alumina and the solution containing the derivative is concentrated by evaporation. The concentrated solution thus prepared is poured into the flow channel of a liquid chromatograph for separating the solution into the components and the fluorescence of catecholamine derivatives is detected.

According to the method of JP-A-60-143776, a vital specimen such as serum or urea is injected into the flow channel and then three types of reaction reagents are introduced successively into said flow channel and during their passage through the reaction coil, the catecholamines are labeled (turned into their derivatives). The labeled catecholamines thus prepared are captured and concentrated by a concentrating column and then transferred into a separating column for separating the components and the fluorescence of the labeled catecholamines is detected.

The method of JP-A-61-88148 is unfit for routine works such as clinical examinations. This is because the method takes time for the operations for preparing the sample to be supplied into the flow channel in a liquid chromatograph and also the automation of the method is difficult. On the other hand, the method of JP-A-0-143766 requires a long reaction coil since after the reagents and sample have been conducted into the carrier liquid flow channel, the sample and the reagents are mixed in the reaction coil during their passage through the coil. Also, this method has the probe that it takes much time until the components are completely turned into the derivatives.

Further, in these prior art methods, no regard is given to cooling of the sample before introduced into a chromatograph.

SUMMARY OF THE INVENTION

A problem that the present inventors were trying to solve is to make it possible to conduct, with certainty, the reaction for turning the components into the derivatives.

Another problem that the present inventors were trying to solve is to compose an apparatus so as to minimize the influence of temperature change on the sample during the reaction.

Still another problem that the present inventors were trying to solve is to facilitate the treatment of a large number of samples.

According to the solution of the problems of the prior art by the present invention, there is provided an apparatus comprising a reaction treating section having disposed therein a reaction vessel which is heated and a sample injection port, and a detachable sample rack set in said reaction treating section. After the lapse of a predetermined period of time from the start of the reaction in said reaction vessel between the reagent and the sample introduced from the sample rack, the reaction mixture in said reaction vessel is transferred to said sample injection port by a suction and discharge nozzle. The reaction vessel may be replaced by a mixing vessel and a flow channel which is heated to a predetermined temperature to allow the reaction to proceed.

According to the other solution of the problems by the present invention, there is provided a method in which the sample is first subjected to a pre-labeling treatment and the labeled sample is passed through a separating column for separating and detecting the components, said method comprising a step of pre-labeling treatment, said pre-labeling treatment including, after a sample rack has been set in position in a body of a labeling apparatus having a mixing vessel which is heated and a sample rack housing portion, supplying a sample and a labeling agent into said mixing vessel by a suction and discharge nozzle to initiate a pre-labeling reaction, and transferring the sample in said mixing vessel to a sample injection port leading to a flow channel in a separating column.

BRIEF DESCRIPTION OF THE DRAWINGS

In the accompanying drawings.

FIGS. 3A and 3B are the diagrams showing operation time schedule of the respective sections in the apparatus of FIG. 1.

DETAILED DESCRIPTION OF THE INVENTION

Figure 1:
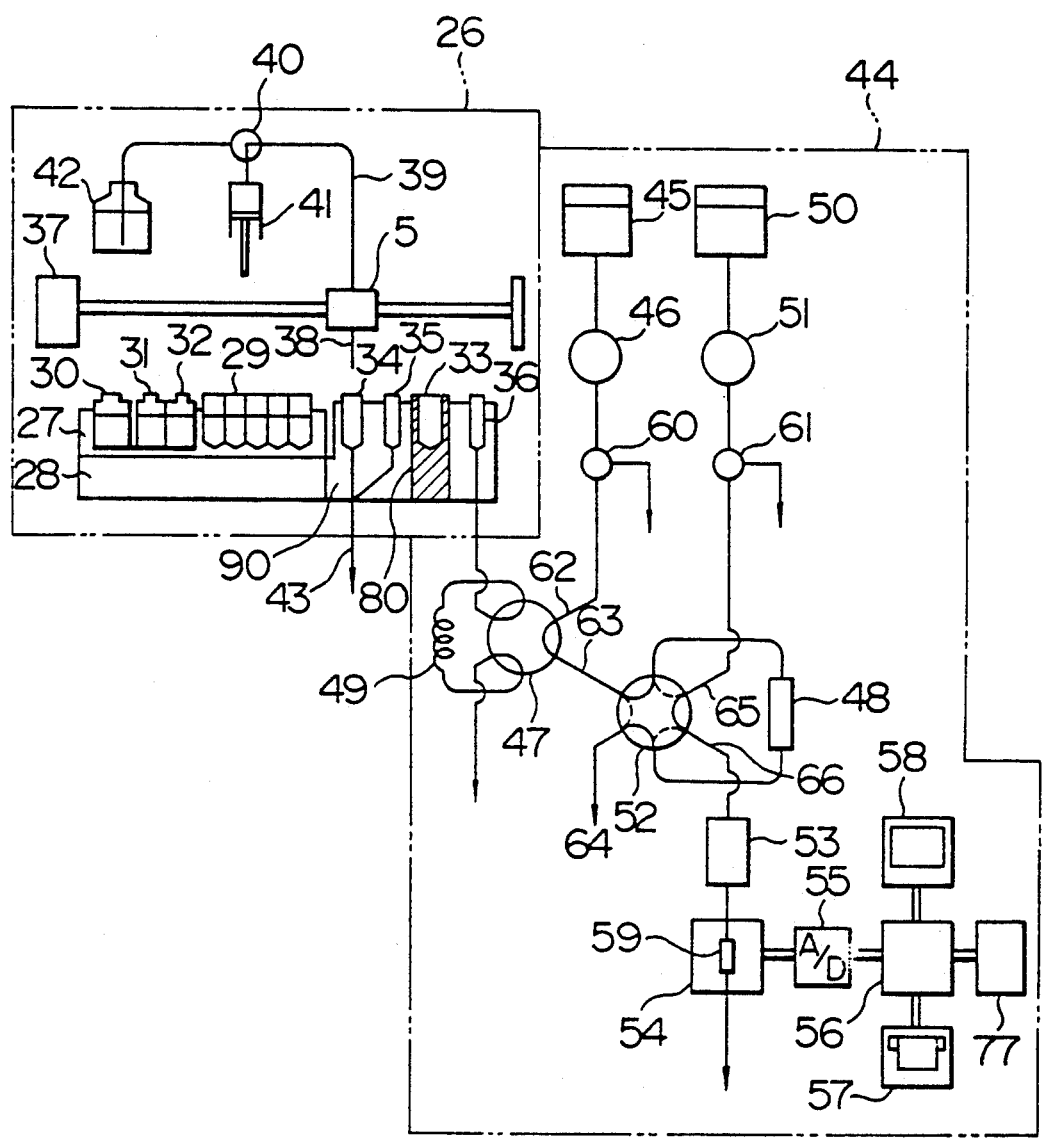
FIG. 1 shows a schematic layout of an apparatus, one embodiment of the present invention.

The reference numerals used in the drawings designate the following parts or elements:

26: auto-sampler, 27: sample rack, 28: sample stage, 29: sample container, 30: reacting reagent container, 33, 79a and 79b: reaction vessel, 35 and 81: drain port, 36: sample injection port, 38: charging nozzle, 47: sample feed valve, 48: pre-column, 49 and 83: metering tube, 52: column switchover valve, 53: separating column, 54: fluorophotometer, 56: control unit, 82: mixing vessel, 85: stop valve, and 90: non-movable portion.

For the analysis of a vital specimen containing catecholamines and other components having similar physical properties, it is expedient to separate and determine the individual components by chromatography. In catecholamines, there are included epinephrine, norepinephrine and dopamine, so that it is possible to determine the concentration of the individual components by separating them by chromatography.

However, it is difficult to detect the catecholamine components in the form as they are in the sample. In the present invention, therefore, catecholamines in the sample are reacted with a labeling agent and made into the derivatives before performing component separation by column chromatography, then the impurities and unnecessary matter such as excess reacting reagent, which could lower detection accuracy, are removed by a pre-column, then the derivatives are introduced into a separating column for separating into the components, and the effluent from the separating column is detected by a detector. In the case where a fluorescent labeling agent is used for the conversion of catecholamines into the derivatives, a fluorescence detector is adapted with utilizing the properties which the components to be detected have acquired as a result of the conversion into the derivative. The detector may be selected from various types of detectors such as absorptiophotometer, conductivity detector, etc., according to the mode of labeling.

The sample feeder, which is also called auto-sampler or labeling apparatus, has a non-movable section and is equipped with a sample rack. The sample rack is set detachably on the non-movable section. The non-movable section may be referred to as the body (portion) of labeling apparatus or reaction treating section. In this non-movable section are disposed a sample injection port, a mixing or reaction vessel, a drain port, etc. Also provided in said non-movable section is a sample rack housing zone which is referred to as sample rack housing portion or sample stage. This section is maintained at a constant temperature usually in the range of 4° to 17° C.

In the case the mixture of the sample and labeling reagent in the mixing container is transferred immediately after mixing to the sample injection port, the mixed solution is first conducted to the flow channel for allowing the reaction to proceed, where the solution is retained for a predetermined period of time until the reaction is substantially completed. In this case, the mixing container need not to be heated but the flow channel is heated to a predetermined temperature.

In case the labeling reaction is carried out on the mixed solution of the sample and the reagent in the mixing container or after transferring the mixed solution to the other container, the mixing container or the other container is heated. This heating is maintained at a constant temperature in the range of 40° to 50° C. In this case, the mixing container or the other container is called reaction vessel.

The sample rack detachably set in the sample rack housing section is provided with a plurality of holes for fixing the sample containers and also has a portion for housing the labeling reagent container. The sample and reagent are cooled on said sample rack housing section.

The sample feeder has a nozzle-moving mechanism and is designed to allow the suction and discharge nozzle to perform various actions. For instance, the suction and discharge nozzle is capable of performing charging of the sample into mixing vessel from the sample container, charging of the reagent into the mixing vessel from the reagent container, stirring of the solution in the mixing vessel by repetition of suction and discharge of the solution, and transfer of the mixed solution to the sample injection port. Since fresh supply of sample is charged successively into the mixing vessel, cleaning of the feeding system is necessary. So, a cleaning fluid is passed through the suction and discharge nozzle and discharged into the mixing vessel from time to time.

In the present invention, since both of the sample and the reagent are charged into the same mixing vessel, the reaction is initiated as soon as they are mixed in said vessel, and the reaction time, which is initiated by the mixing of the sample and the reagent and is terminated with the transfer of the reaction solution to the sample injection port, can be exactly determined by controlling the timing of operation of the suction and discharge nozzle. Since the mixing is performed in a vessel, homogenization of the mixed solution is promoted.

In the case a vital sample is used, the sample is cooled for preventing its degeneration. For promoting the labeling reaction, it is expedient to heat the reaction vessel. However, if the heating temperature is influenced by the cooling means of the sample, the reaction temperature may fluctuate, making it hard to keep the reaction conditions constant. In the present invention, since the reaction vessel is set apart from the sample rack and a heat insulator can be readily provided therebetween, it is possible to maintain the stable reaction conditions. Further, since the sample rack is designed to be detachable from the reacting section, it is possible to feed the sample and/or reagent into the sample rack beforehand and then set the sample rack in an analyzer for carrying out the analyses, or to take away the analyzed sample with the rack.

As a fluorescent labeling agent serving as a reagent for turning catecholamines into the derivatives, there can be used, for example, 1,2-diphenylethylenediamine (DPE). The solution of fluorescent labeling agent to be prepared contains 60 mM of DPE, 2 mM of potassium ferricyanide and 40% of acetonitrile. As the eluting solution supplied into the separating column for separating catecholamines into the components, there is used, for example, a fluid containing acetonitrile, methanol and an aqueous solution in a ratio of 5:2:4, where the aqueous solution contains 50 mM of lithium nitrate and 10 mM of sodium dodecylsulfate.

An example of automatic catecholamine analyzing apparatus of the present invention is described below with reference to the drawings.

FIG. 1 is a schematic layout of the automatic catecholamine analyzing system. The system has a sample feeding section 26 in which various types of containers and charging mechanism are provided and a concentrating and separating section 44 in which concentration and separation of the sample are performed in the respective flow channels. Hereinafter, the sample feeding section 26 is referred to as auto-sampler and the concentrating and separating section 44 as analyzing section The auto-sampler 26 has a non-movable portion or a reaction treating portion 90 and is also provided with a detachable sample rack 27.

Said sample rack 27 is set at a sample stage 28 in the auto-sampler 26 and holds a plurality of sample containers each containing a sample of plasma. In said sample rack 27 are also disposed a reaction reagent container 30 for fluorescent labeling, an internal standard liquid container 31 and a standard sample container 32. At the fixed positions on the non-movable portion 90 close to the sample stage 28, there are provided a reaction vessel 33, a nozzle cleaning tank 34, a drain port 35 and an injection port 36.

Suction and discharging nozzle 38 has the functions of charging the sample and reagent into the reaction vessel 33 by a pipet and transferring the reacted sample to the injection port 36 from the reaction vessel 33. Driving mechanism 37 has a function to move the nozzle 38 along the x-, y- and z-axes which cross vertically each other. The mechanism enables to move the nozzle 38 freely in three-dimensions so that the nozzle can be positioned at the container or the port on said auto-sampler. The upper end of said nozzle 38 is connected to a charging pump 41 and a cleaning fluid tank 42 through a fine tube 39 such as plastic tube and a three-way valve 40. In this invention, a syringe pump driven by a pulse motor is used as charging pump 41. Thermostatic block 80 is provided for maintaining the temperature of reaction vessel 33 at a prescribed level. In the sample stage 28 is incorporated a cooling means which keeps the sample and reagent on the sample rack 27 at a low temperature during the analysis.

The analyzing section 44 consists of a pre-column flow system in which the sample is concentrated and the impurities are removed, a separating column flow system in which the sample is separated into the components, and a metering and operating unit. In the pre-column flow system, a cleaning fluid in its storage tank 45 is led out to flow at a constant rate by a pump 46 and sent into a pre-column unit 48 through a sample introducing valve 47. Also connected to said sample introducing valve 47 is a metering tube 49 by which the flow of the sample solution injected from the injection port 36 is regulated so that a determined amount of sample solution is introduced into the analyzing section.

In the separating column flow system, an eluting solution in its reservoir 50 is led out to flow at a constant rate by a pump 51 and sent into a single separating column 53 through a column change-over valve 52. This column change-over valve 52 may be switched so that the eluting solution passes through the pre-column 48 to transfer the sample treated in said pre-column 48 to the separating column 53. The metering and operating system comprises a fluorophotometer 54 for measuring the strength of fluorescence of the sample components eluted from the separating column 53, an A/D converter 55 which performs operational processing and display of the determination results, a control unit 56, a printer 57, CRT 58, etc. Said fluorophotometer 54 has a flow cell 59. Change-over valves 60 and 61 are designed to be capable of purging the liquid in the pumps 46 and 51, respectively, when such is necessary.

In the instant example of the present invention, the analysis is performed by conducting the following operations successively:

(1) Fluorescent labeling of the sample on the auto-sampler.

(2) Concentration and removal of impurities by the pre-column.

(3) Separation and determination of the sample components by the separating column.

Figure 2:
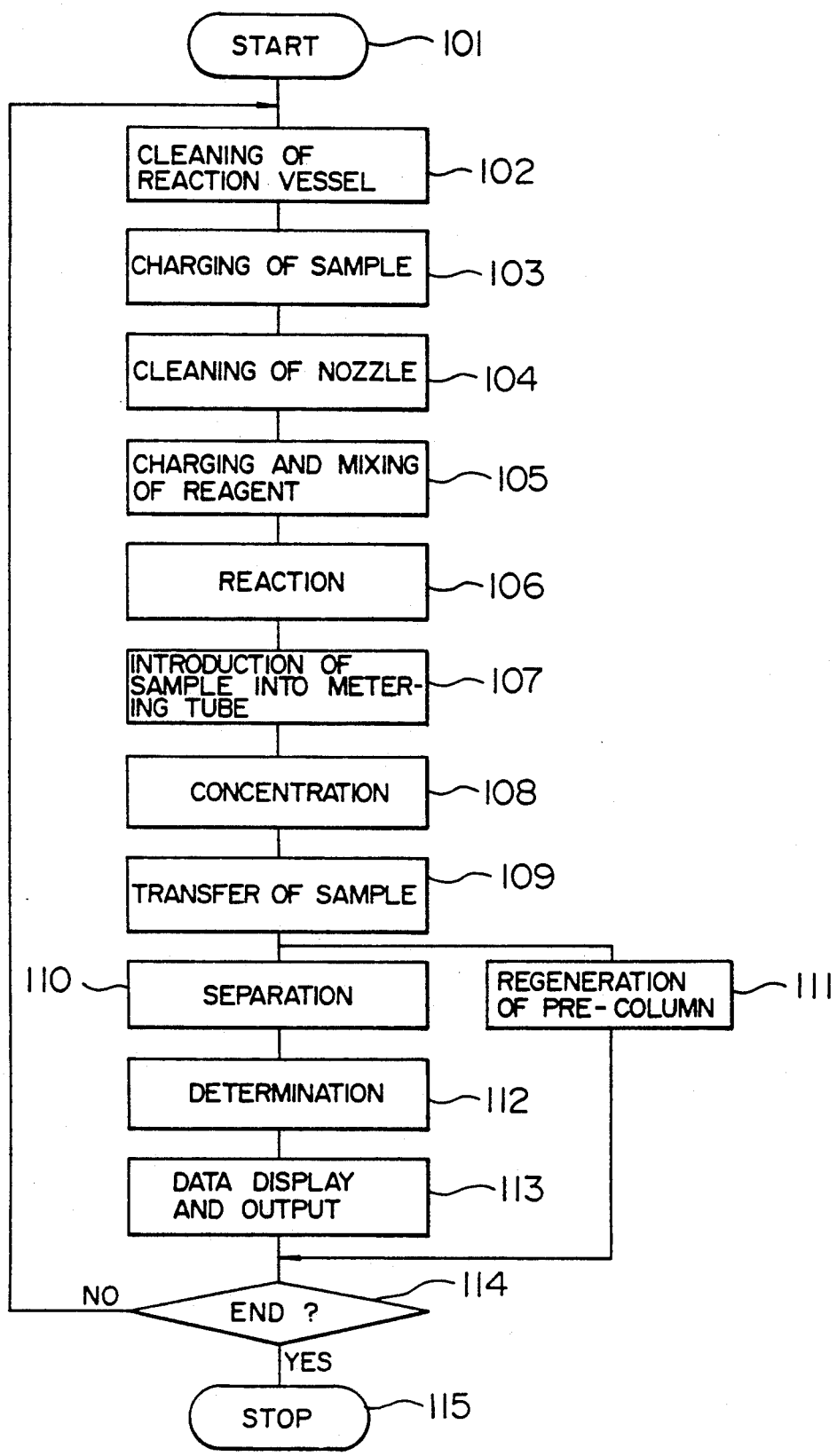
FIG. 2 is a flow sheet of the analyzing process in the apparatus of FIG. 1.

The series of analyzing operations are explained below by referring to the flow chart of FIG. 2.

Cleaning of Reaction Vessel

After indicating the start of the analyzing process at step 101, reaction vessel 33 is cleaned at step 102. In this step, nozzle 38 is moved to the position of reaction vessel 33 and pump 41 is operated to supply the cleaning fluid from its storage tank 42 into the reaction vessel. The cleaning fluid is supplied in a greater amount than the capacity of reaction vessel 33, with the overfluous cleaning fluid being overflown and passed into discharge pipe 43 through drain port 35. Then, nozzle 38 is lowered down to the position of the bottom of reaction vessel 33 to suck up the used cleaning fluid in the vessel and then moved to the position of drain port 35 to discharge the sucked-up fluid therethrough. Prior to this operation, a small amount of air has needed to be sucked up and left in the end of nozzle 38 so that the used dirty fluid sucked up by said nozzle be diffused into the fresh cleaning fluid in the same nozzle. (The operation of sucking up air to form a boundary with air cells before suction of the used fluid needs to be performed when sucking up the sample and reagent in the later step, but no explanation on this operation is given in the following descriptions for avoiding complication of the explanation.) The above- described series of operations are repeated a suitable number of times (for example, three times) to accomplish cleaning of reaction vessel 33.

Charging of Sample

The sample is charged into reaction vessel 33 in step 103. Nozzle 38 is first moved to the position of internal standard solution container 31, lowered down thereinto to suck up a determined amount of solution, raised up from said container 31, then moved to the position of sample container 29 to suck up a determined amount of the sample to be analyzed, and then further moved to the position of reaction vessel 33, and there the sample and internal standard solution held in the nozzle are charged into said reaction vessel 33. The internal standard solution is a standard solution used for correcting variation of percent recovery from the column and other matters In this example of the present invention, isoproterenol is used as a standard material.

Cleaning of Nozzle

Nozzle 38 is cleaned in step 104. Nozzle 38 is moved to the position of drain port 35 and the cleaning fluid is discharged out through the nozzle to clean out contamination on the inner wall of nozzle 38 due to the internal standard solution and the sample. Then the nozzle is further moved to the position of cleaning cistern 34 and lowered down thereinto and the cleaning fluid is discharged out to clean the outside of the fore end of nozzle 38.

Charging and Mixing of Reagent

The reagent is added into reaction vessel 33 in step 105. Nozzle 38 is moved to the position of reacting reagent container 30 and a prescribed amount of the derivative-forming reagent is sucked up into the nozzle. This reagent is then injected into reaction vessel 33 and mixed with the sample and internal standard solution which have been previously supplied into said reaction vessel. Mixing can be alternatively effected by the other methods, for example, a method comprising sucking up air in the nozzle, inserting the nozzle into the reaction vessel and discharging air in the nozzle into the vessel, or a method comprising shaking or vibrating the reaction vessel by an external mechanical or electrical means. If the reagent is a liquid easily miscible with the sample and internal standard solution, and the discharge is conducted in a relatively large amount, it may sufficient to merely discharge out the liquids at a high speed.

Reaction

In step 106, a fluorescent labeling reaction is carried out for effectuating conversion of catecholamines into the fluorescent substances (derivatives). The mixed solution of the sample and the converting reagent in reaction vessel 33 (hereinafter referred to as sample solution) is left in reaction vessel 33 kept at a fixed temperature for a predetermined period of time to allow the reaction to proceed, thereby effectuating fluorescent labeling.

Introduction of Sample Into Metering Tube

The reacting solution in reaction vessel 33 is introduced into metering tube 49 in step 107. The sample solution containing catecholamines which have substantially undergone the labeling reaction in reaction vessel 33 and turned into the derivatives is sucked into nozzle 38. This nozzle is moved to the position of injection port 36 and inserted thereinto, and the sample solution is injected into sample metering tube 49 by setting sample introducing valve 47 in the state shown in FIG. 1. When said valve 47 is switched after metering tube 49 has been filled with the sample solution, metering tube 49 connected to a port of change-over valve 47 is connected between flow channel 62 and flow channel 63 and a prescribed amount of sample solution is transferred into pre-column 48 by the flow of the transferring and cleaning fluid.

Concentration

In step 108, capture of catecholamines in the form of the derivative in pre-column 48 and removal of impurities and excess reagent are performed. Concentration of the sample solution is conducted. As the sample solution is introduced into pre-column 48 by the flow of the transferring and cleaning fluid, the sample is captured by adsorption and accumulated in pre-column 48. The matters which disturbs the determination, such as impurities and excess reagent, are passed through the pre-column and discharged out from discharge port 64.

Transfer of Sample

In step 109, the sample cleared of unnecessary matter and captured in pre-column 48 is led out therefrom and conducted into separating column 53. When column change-over valve 52 is switched from the state shown by solid lines in FIG. 1 to the state shown by broken lines, pre-column 48 is connected between flow channels 65 and 66, allowing the eluting solution to flow through pre-column 48, whereby the concentrated sample in pre-column 48 is dissociated and transferred into separating column 53. When column change-over valve 52 is again switched (to the solid-line state in the drawing) at the point when the whole sample has been passed into flow channel 66, the eluting solution is allowed to flow directly into separating column 53 without passing through pre-column 48, and the transferring and cleaning fluid begins to flow into pre-column 48.

Separation

In step 110, the eluting solution is kept flowing into separating column 53 where the separation of the components derived from catecholamines is conducted and consequently norepinephrine (NE), epinephrine (E), dopamine (DA), etc., form the component bands and are eluted from the separating column.

Regeneration of Pre-Column

In step 111, the transferring and cleaning fluid is flown into pre-column 48 synchronously with sample component separation in step 110, and pre-column 48 is regenerated into a state ready for receiving the next supply of sample.

Determination

In step 112, the eluates from separating column 53 are observed by fluorophotometer 54. The sample components separated and eluted from separating column 53 flow successively into flow cell 59 in fluorophotometer 54 and the strength of fluorescence of each separated component is detected and subjected to arithmetic operations to determine the concentration of each component.

Data Display and Output

In step 113, the data obtained in step 112 are displayed and output by using printer 57, CRT 58, etc. In step 114, it is judged whether all the samples on auto-sampler 26 have been subjected to the schemed process. If there still remains an unprocessed samples, it is brought back to step 102 and subjected again to the above-described sequential steps for analysis. When it is confirmed that all the samples have duly undergone the above steps, the process proceeds to step 115 to stop the analyzing operations of the apparatus.

The analyzing procedure for one sample according to the present invention has been described above. In the following, there will be described the procedure of continuous analyzing operations for a plurality of samples. FIGS. 3A and 3B show an example of analysis program in performing continuous analyzing operations.

On the vertical axis in the drawing, the operations in the above-explained flow chart of analysis are divided into three steps or divisions according to the items of operation. The first step comprises principally the operations for turning catecholamines into the derivatives on an auto-sampler. The point of the second step is concentration of the sample by a pre-column. The third step covers the operations for separating and determining the sample components by a separating column. The boundaries between the respective steps of operations were decided so that the time allocation for the respective steps would suit the scheduled analysis program. The number of cycles and time used for the respective operations in the progressing analysis program are shown on the horizontal axis. The program was worked so that one round of operations from the first to third steps be completed in one cycle.

FIG. 3A shows an analysis program focussing on the state of analysis (indicated by bald solid lines) of the nth sample. Fine solid lines indicate the operating timing for the analysis of (n+1)th sample and (n−1)th sample, and broken lines indicate the operation timing for the analysis of (n−2)th sample and (n+2)th sample. FIG. 3B shows the operation timing of the change-over valve. The "metering" state a of sample introducing valve 47 is the state in which the sample solution can be injected into metering tube 49 from injection port 36, namely the state shown in FIG. 1. The "transferring" state b is the state in which the valve was switched to connect metering tube 49 to the pre-column flow channel. The "connecting" state c of column change-over valve 52 denotes the state in which pre-column 48 was connected to the separating column flow channel. The "synchronous treating" state d refers to the state in which the transferring and cleaning fluid is flown concurrently with the sample component separating operation. This state is indicated by solid lines in FIG. 1. The switching action of each change-over valve is repeated for every cycle of operations.

In practice of continuous runs of analysis, a round of analyzing operations are conducted on the first sample (the sample analyzed at first) in the first cycle. This is followed by the second and succeeding cycles of analyzing operations on the second and succeeding samples on the auto-sampler. FIG. 3A shows the operating program in the nth to (n+2)th cycles. It will be noted that in the nth cycle, the analysis of the nth sample (the sample analyzed in the nth place) is started and the operations in the first step are conducted. This is synchronized with the previously-started operations in the second step on the (n−1)th sample and with the operations in the third step on the (n−2)th sample. In the (n+1)th cycle, the nth sample proceeds to the operations in the second step and the succeeding (n+1)th sample is subjected to the operations in the first step. This is synchronized with the operations in the third step on the (n−1)th sample. Further, in the (n+2)th cycle, the nth sample now proceeds to the third step of analyzing operations while the (n+1)th sample undergoes the operations in the second step. Concurrently with this, the operations in the first step are conducted on the succeeding (n+2)th sample.

In the case only one sample is analyzed, the time required for the analysis with the present apparatus is the sum of the times required for the first, second and third steps. However, in the case three samples are analyzed concurrently and successively, it is possible to savetime for analysis. In the present example, it takes 15 minutes to complete the analysis, so that the treating time per sample is 5 minutes.

In chromatographying catecholamines, it is desired to chromatograph at least 10 samples per hour, so that the time allowed to spent for a sample is 6 minutes or shorter.

Figure 4:
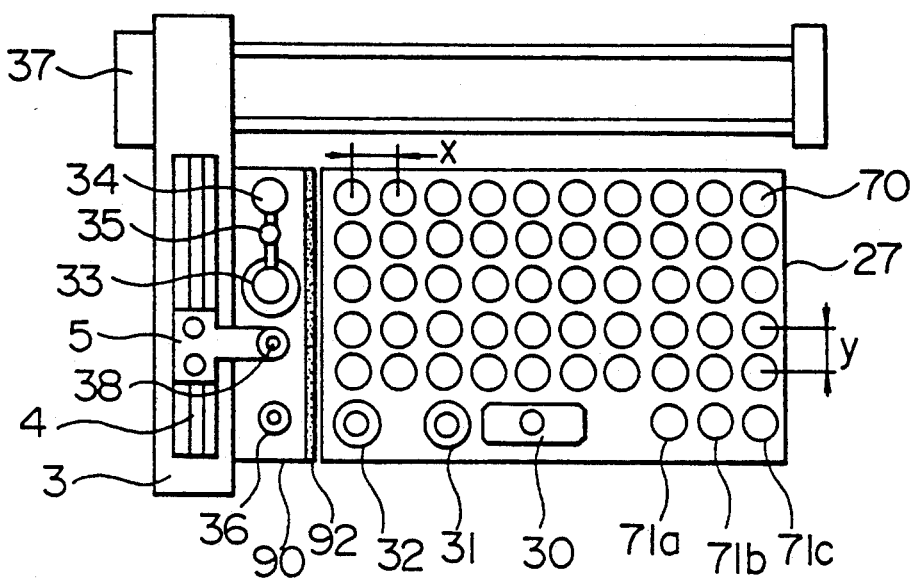
FIG. 4 is a top plan of the auto-sampler in the apparatus of FIG. 1.

FIG. 4 is a plan view of auto-sampler 26 in the analyzing apparatus of FIG. 1. Sample rack 27 is detachably mounted on sample stage 28. Said sample rack 27 has formed therein sample container holding holes 70, arranged in columns of 10 and in files of 5, totalling 50, in the form of matrix. The sample containers each containing a sample to be analyzed are placed and held in these holes 70. On said sample rack 27 are also provided the receptacles for reaction reagent 30, internal standard solution 31 and standard sample 32 as well as emergency sample container holding holes 71a, 71b, 71c for allowing emergent cut-in determination during analysis. On one side of said sample rack 27, there are provided reaction vessel 33, nozzle cleaning cistern 34, drain port 35 and injection port 36 connecting to metering tube 49, each at the fixed position. Charging nozzle 38 is secured to a holding portion 5 arranged slidable on shaft 4 of a moving block 3. Driven by a driving mechanism 37, said nozzle 38 can be moved freely in three-dimensions along the directions of x-, y- and z-axes so that it can be moved to the position of any of said containers or ports for performing the necessary works. Heat insulating member 92 is disposed between non-movable portion 90 and sample rack 27.

The analyzing process is started as the operator pushes the analysis starting switch on control panel 77 after said sample rack 27 carrying the samples to be analyzed and reagent has been set in position on sample stage 28 of auto-sampler 26.

Figure 5:
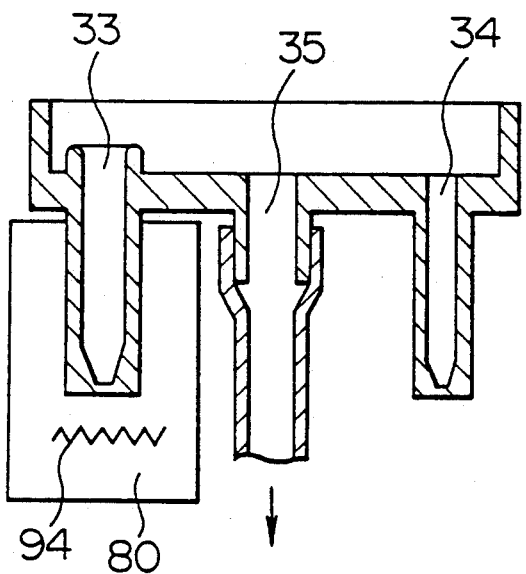
FIG. 5 is an enlarged longitudinal sectional view of a drain port and the neighboring parts in a section of FIG. 4.

FIG. 5 is a sectional view of reaction vessel 33, nozzle cistern 34 and drain port 35. Since it is necessary to wash every sample supplied into reaction vessel 33, there is employed here an overflow system in which the washing liquid is ejected from the nozzle end to pass through the reaction vessel from its bottom and discharged out automatically from its top. The washing effect is enhanced by forming a flow from one direction as described above. Thermostatic block 80 is incorporated with a heater 94. Reaction vessel 33 is also designed to serve as a mixing container. Further, reaction vessel 33 is kept at a constant temperature in the range of 40°–50° C. (for example, at 45° C.) by thermostatic block 43 to promote the reaction.

Thermostatic arrangement is aimed at improving reproducibility of the reaction conditions. It is designed to keep the reaction conditions constant no matter whether the analysis is conducted at any season of the year or at any time of the day so that the obtained data can always be compared in the same light. The reason for maintaining the temperature constant at 40°-50° C. is as follows. Firstly, regarding maintenance of temperature above 40° C., since it is assumed that the room temperature condition for setting the apparatus is 15°-35° C., said temperature setting (above 40° C.) is necessary for stable control of reaction as there is a possibility of rise of temperature in the apparatus above said assumed temperature range of 15°-35° C. As for setting of temperature below 50° C., though the reaction is promoted when the temperature is high, a temperature above 50° C. may cause denaturation of the sample, so that said temperature setting (below 50° C.) is intended for preventing occurrence of such denaturation of the sample and for protecting the operator from suffering from a burn even if he or she should touch the reaction apparatus.

As shown in FIG. 4, sample rack 27 is square-shaped and has formed therein sample container receiving holes 70 which are arranged regularly in rows of 10. This is intended to allow easy counting of the sample number by the operator. In the example shown in FIG. 4, said sample container receiving holes are formed in five rows, each row consisting of 10 holes. The interval y between the center of a hole in a row and the center of the adjoining hole in the adjoining row is 15-25 mm. This interval is designed to allow the operator to insert his or her fingers so that he or she can easily grip a sample container when it is placed in or taken out of the sample rack. As for the size of sample rack 27, a smaller size provides a greater convenience for handling thereof. For this reason, the interval x between the center of a hole and the center of the adjoining hole in a same row is made smaller than y. For instance, it may be less than 12 mm.

Figure 7:
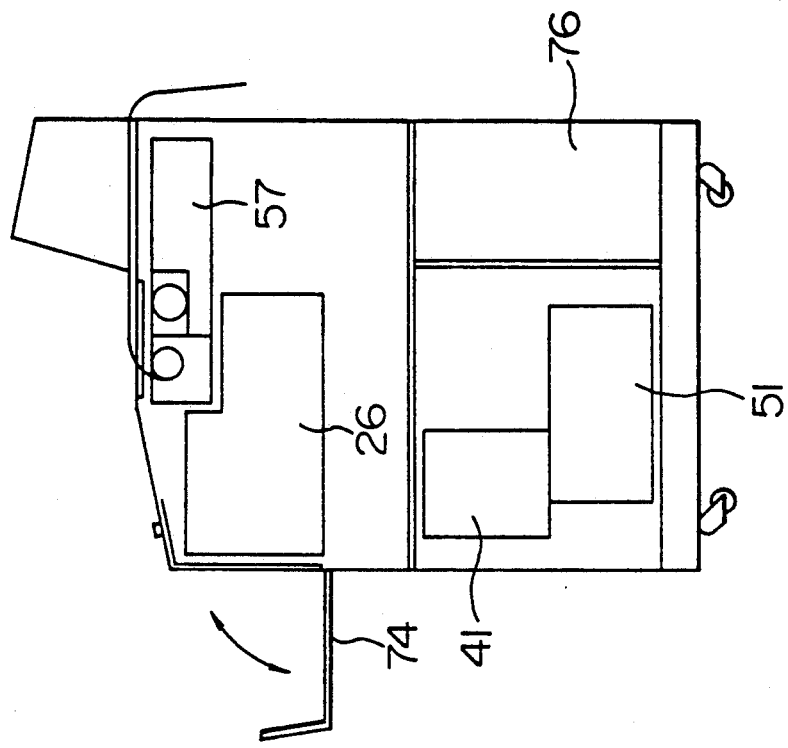
FIG. 7 is a schematic view of arrangement of parts as taken sidewise of FIG. 6.
Figure 6:
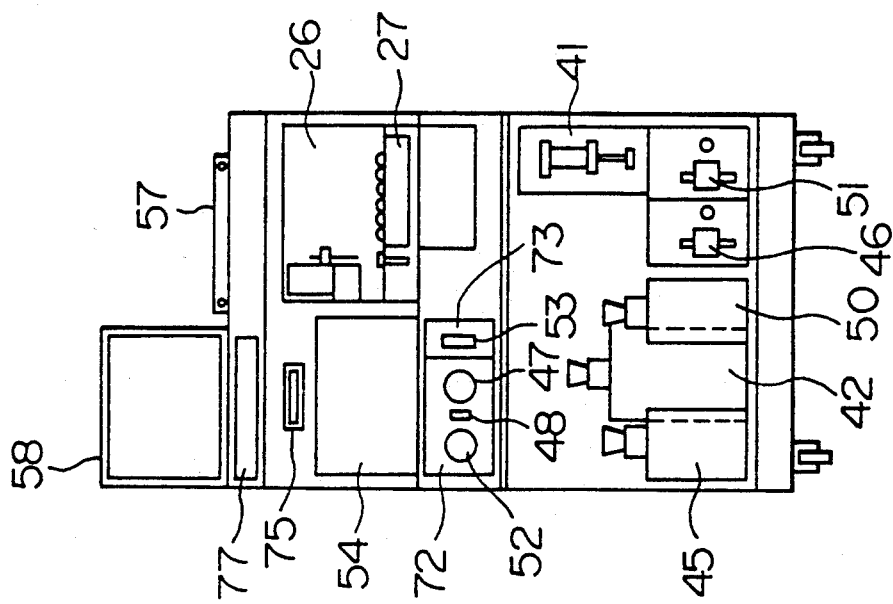
FIG. 6 is a frontal external appearance of the apparatus of FIG. 1.

FIGS. 6 and 7 show a general external appearance and positional relation of the principal parts of the apparatus in the example shown in FIG. 1. This catecholamine analyzer is a vertical type and has incorporated therein all the units necessary for the analysis.

The apparatus is partitioned into two stages. In the upper stage are disposed auto-sampler 26, fluorophotometer 54 and column panel 72. On column panel 72 are disposed pre-column 48, separating column 53, sample introducing valve 47 and column change-over valve 52. Separating column 53 is controlled in temperature by thermostatic block 73 for keeping the temperature constant at a specified level during analysis. Mounting and demounting of sample rack 27 to and from auto-sampler 26 are practiced by opening or closing cover 75. Floppy disc 57 for storing data of determinations is set above fluorophotometer 54.

In the lower stage of the apparatus are disposed cleaning fluid tank 42, transferring and cleaning liquid tank 45, eluting solution tank 50, charging pump 41, pump 46 for the transferring and cleaning liquid, and pump 51 for feeding the eluting solution. The liquids necessary for the analyzing units in the upper stage of the apparatus are supplied from the lower stage. Electric unit 76 including power source, substrates, etc., is housed in a rear portion of the lower stage of the apparatus. On the top of the apparatus are disposed printer 57, CRT 58 and control panel 77 for performing input operations for the analyses by this apparatus.

Figure 8:
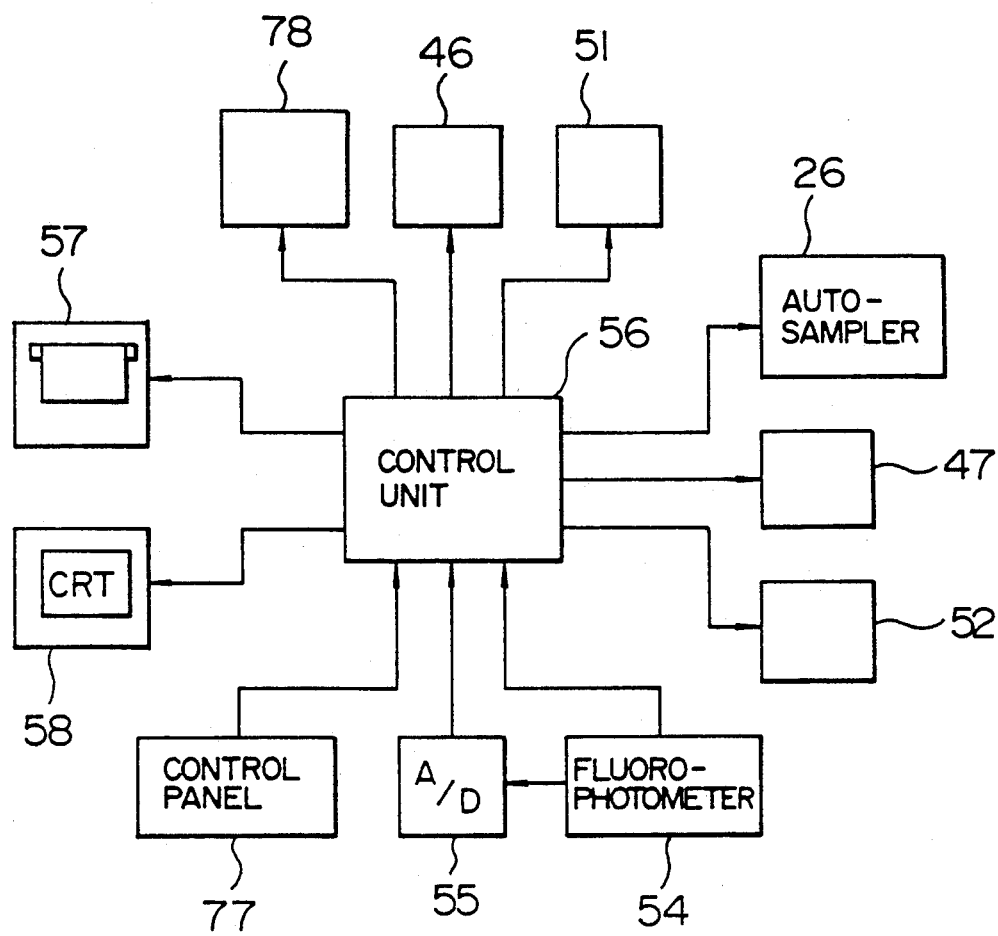
FIG. 8 is a control system diagram of the apparatus of FIG. 1.

FIG. 8 shows the control system in the present example of the invention. Control of the analyzing operations by the apparatus is made with control unit 56 as the hub of the system on receiving input signal from control panel 77. In operation, when the power switch is turned on, temperature control device 78 is operated and the light source of fluorophotometer 54 goes on. Then the analysis standard switch is turned on to operate pumps 46 and 51 to start supply of liquids. After setting sample rack 27 in position on auto-sampler 26, the analysis starting switch is turned on to operate auto-sampler 26, sample introducing valve 47 and column change-over valve 52 to start the series of analyzing operations which are conducted according to the procedure explained above with reference to FIGS. 2 and 3. The result of determination is transmitted as a signal from fluorophotometer 54 through A/D converter 55 into control unit 56 where the signal undergoes data processing and the obtained information is printed out by printer 57 and displayed on CRT 58.

Figure 9:
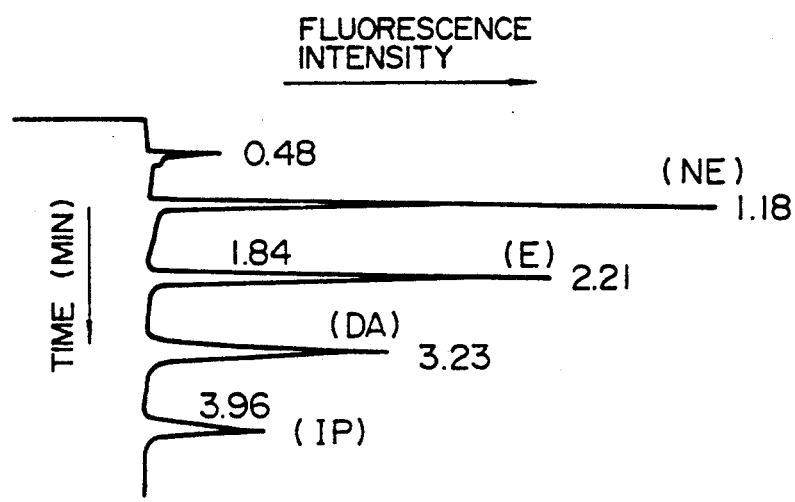
FIG. 9 is a scheme showing a mode of analysis of a catecholamine.

FIG. 9 shows an example of the result of analysis of catecholamines by the above-described system. The numerical value given at each peak indicates retention time, namely the time spent from the start of separation to the pass of the separated component through the detector. In this system, the start of separation is the time point at which column change-over valve 52 is switched to start transfer of the concentrated sample in pre-column 48 to separating column 53. The first peak of 0.48 second was detected as the transferring fluid stored in the pre-column has passed the detector prior to the detection of the separated and eluted sample components. Then the sample components separated by separating column 53 are eluted in the order of norepinephrine (NE), epinephrine (E) and dopamine (DA), and finally the internal standard substance, isoprotenol, added as internal standard solution is eluted and detected. The concentration of each component is determined from the corresponding peak area.

In the case of this example of analysis, the schemed separation was completed in a little over 4 minutes after start of separation, namely after switching of column change-over valve 52. Thus, this example of analysis enables sample separation within 5 minutes per sample as explained above.

In the case of using this system of analysis, the sample numbers and the signals and concentrations of the three analyzed components are printed out by printer 57, and the chromatogram such as shown in FIG. 9 can be displayed on CRT display or printed out as desired.

Also, although a single pre-column is used in the above-described embodiment of the invention, there are the cases where a plural number of columns are used. In such a case, for example, two pre-columns are used by arranging them in series to divide the work of removing water-soluble impurities and the work of removing hydrophobic impurities.

Figure 10:
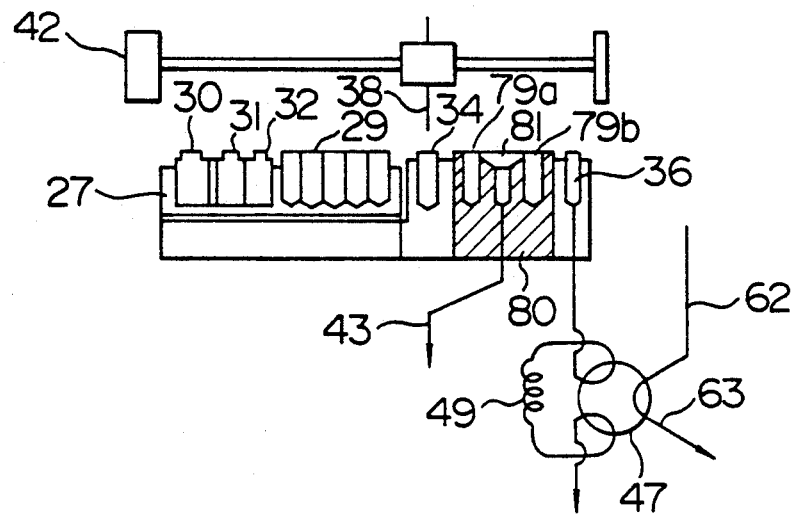
FIG. 10 is a schematic illustration of setup of the principal parts in a first example of modification of the apparatus.
Figure 11:
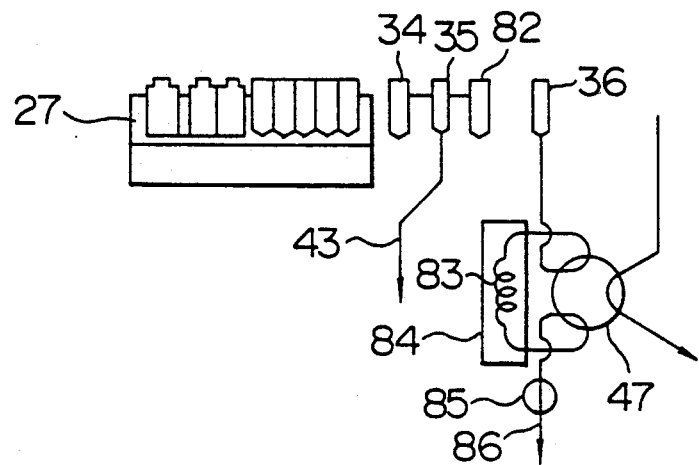
FIG. 11 is a schematic illustration of setup of the principal parts in a second example of modification.
Figure 12:
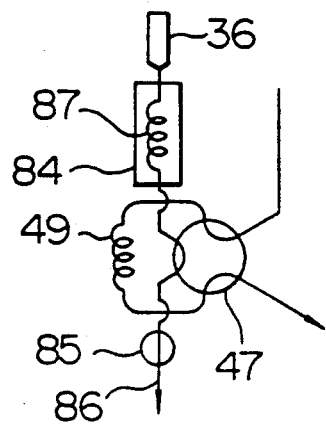
FIG. 12 is a schematic illustration of setup of the principal parts in a third example of modification.

FIGS. 10, 11 and 12 show the different ways of carrying out the reaction for converting catecholamines in the sample into the derivative.

In the first modification shown in FIG. 10, there are used two reaction vessels. In this case, two reaction vessels 79a, 79b are provided on the auto-sampler, each vessel being controlled in temperature by thermostatic block 80. Also, at the time of cleaning of the reaction vessels, the overflowing cleaning fluid is let flow into drain port 81. This system is suitably employed in the case the operations for forming derivatives on the auto-sampler (namely the operations in the first step described above) take a longer time than the intended time for one cycle for the reasons that the reaction takes much time etc. According to this system, it is possible to complete the treatment of sample within the cycle of operations by charging two sets of the sample and reagent into the two reaction vessels alternately and supplying one reacted sample within the time interval of one cycle. When the reaction time needs more than two times longer than the period of one cycle, it may be sufficient to increase the number of reaction vessels. In any case, the reaction vessels are used repeatedly periodically.

The first modification includes another way of utilization. That is, one (79a) of the two reaction vessels is used as mixing vessel, and each time mixing has ended, the mixed solution is transferred into another reaction vessel 79b. The merit of this method is that the reproducibility of the reaction can be advantageously maintained since the sequence of operations, the mixing conditions and the reaction conditions including reaction temperature are regularized.

FIG. 11 shows a second modification where the reaction is performed in the metering tube associated with the sample introducing valve. Container 82 on the auto-sampler is used as mixing container for mixing the sample and reagent. The solution, in which the sample and reagent begin to react as soon as they are mixed, is charged into metering tube 83 from charging port 36 by using charging nozzle 38. In said metering tube 83, the solution is left stagnant for a predetermined period of time and allowed to react. Metering tube 83 is kept at a fixed temperature by thermostatic block 84. Also, stop valve 85 is provided in the discharge channel so that the solution is allowed to stand still during the reaction. This system cannot be employed for long-time reactions since the reaction time is determined by the acting interval of sample introducing valve 47. However, as metering tube 83 is made by coiling a synthetic resin tube or the like, this system has the advantages of easy temperature control and a high degree of freedom for spacing design. For example, the separating column can be integrated with the thermostatic block.

Figures 13A, 13B:
FIGS. 13A and 13B are the diagrams showing operation time schedule of the respective sections in an analyzer applied to the modification shown in FIG. 11.

FIGS. 13A and 13B show one example of operation program in the second modification shown in FIG. 11. This program, like that of the previous example shown in FIG. 3, is roughly divided into three steps in which step 1 comprises the operations on the auto-sampler for the derivative, step 2 comprises the concentration works by a pre-column and step 3 comprises the separating and determining operations by a separating column. However, the boundaries of operations between the respective steps are slightly different from those in the program of FIG. 3. That is, in the present program, the first step ends with injection of the sample solution into metering tube 83 through sample introducing valve 47, and the second step begins with initiation of the reaction in the metering tube and ends with concentration of the sample by a pre-column, and the third step starts with transfer of the sample in the separating column. Thus, in the examples shown in FIG. 11, either, the operations for the analysis can be roughly divided into three types of works, namely the works by the auto-sampler, the works by the pre-column and the works by the separating column. The respective works can be conducted synchronously on the samples to be analyzed continuously according to the program and repeated.

The third embodiment shown in FIG. 12 is of a system in which reaction coil 87 is provided in the flow path running from sample injection port 36 to sample introducing valve 47, and the sample solution is injected into said reaction coil for conducting the reaction, after which said sample introducing valve is switched to lead the reacted sample solution into metering tube 49 and then valve 47 is again switched to conduct the solution into the analyzing unit. This system leaves much more time for reaction in reserve as compared with the previous modification but is complicated in operations since the sample solution must be transferred in two stages.

While the present invention has been described concerning the examples of automatic analyzer for catecholamines, the scope of application of this invention is not necessarily limited to these examples. For instance, the principle of the present invention can be applied to the analysis of various kinds of substances beside catecholamines, such as amino-acids, bile acid, guanidine, etc. Also, as regards the method for making a derivative and detector used for determination, although a method using a fluorophotometer is employed in the described examples of the invention, it is possible to apply other analyzing methods using an ultraviolet or visible light photometer according to enzymatic or UV activation techniques. Further, regarding concrete means for effecting conversion of catecholamines in the sample into the derivative, various changes and modifications are conceivable relating to the site of reaction, procedure of operations, programming and other matters.

As described above, the present invention makes it possible to perform the pre-labeling treatments in liquid chromatography with excellent reproducibility and can contribute to automation of the inspection works.

What is claimed is:

1. A liquid chromatographic analyzer which comprises:
   (i) a reaction performing section having a reaction vessel equipped with a heating means, a sample injection port through which a sample is introduced and a suction and discharge nozzle freely movable in three-dimensions,
   (ii) a sample rack for carrying samples containing components for analysis and a pre-labeling reagent for the components, said rack is detachably set in the reaction performing section and arranged in the proximity of the reaction vessel and the sample injection port, said suction and discharge nozzle moving along a path extending from the sample rack to the sample injection port,
   (iii) a separating column for separating a sample containing pre-labeled components for analysis into sample components and
   (iv) a detector for detecting the separated components,
   the reaction vessel serving to react the pre-labeled reagent with the sample transferred form the sample rack via said suction and discharge nozzle for a predetermined period of time to obtain a reaction mixture, and
   the suction and discharge nozzle serving to transfer the reaction mixture form the reaction vessel to the separating column through the sample injection port.

2. The analyzer of claim 1, wherein the reaction vessel is controlled at a temperature of 40° to 50° C.

3. The analyzer of claim 1, wherein the reaction performing section has an area for housing the sample rack which area is controlled at a temperature of 4° to 17° C.

4. The analyzer of claim 1, wherein the sample rack has sample container holding portions and a portion for holding a container for the pre-labeling reagent.

5. The analyzer of claim 4, wherein the sample container holding portions include rows of holes, each row being consisting of 10 holes.

6. The analyzer of claim 5, wherein the interval between the rows of holes is greater than the interval between the holes in the same row and the interval between the rows of holes is 15 to 25 mm.

7. The analyzer of claim 1, which further comprises a metering tube provided between the sample injection port and the separating column and a flow pass switching means for communicating the sample injection port with the metering tube at the time of introduction of the sample.

8. A liquid chromatographic analyzer which comprises:
   a mixing vessel for mixing a sample containing components for analysis in a pare-labeling reagent to obtain a mixed solution,
   a sample injection port through which the mixed solution is introduced,
   a pre-column for capturing the introduced mixed solution and a concentrating solution to obtain a concentrated mixed solution,
   a separating column for separating the concentrated mixed solution into sample components,
   a suction and discharge nozzle for transferring the mixed solution to the pre-column through the sample injection port, said suction and discharge nozzle being movable from said mixing vessel to said sample injection port,
   a flow channel disposed between the sample injection port and the pre-column, the temperature of the flow channel being controlled to have a prescribed temperature, and
   means for retaining a flow of the mixed solution in the flow channel for a prescribed period of time in order to cause a pre-labeling reaction between the sample and the pre-labeling reagent.

9. The analyzer of claim 8, which further comprises:
   a heating means for heating the mixing vessel,
   a sample rack housing portion equipped with a cooling means, and
   means for supplying a cleaning fluid into the vessel, the sample rack housing portion and the vessel being thermally insulated from each other,
   the sample injection port, the vessel for mixing the sample, the sample rack housing portion and the means for supplying a cleaning fluid forming a sample feeder.

10. The analyzer of claim 9, which further comprises a drain port for discharging a waste liquid,
    the sample injection port, the vessel and the drain port being arranged in a straight line.

11. The analyzer of claim 9, which further comprises:
    a sample rack for carrying a sample and reagents used for analysis which rack is set in position in the sample rack housing portion, and
    the nozzle also serving as a means for supplying the cleaning liquid into the vessel.

12. A catecholamine analyzer comprising a non-movable section including a sample injection port, a reaction vessel equipped with a heating means and a rack mounting portion arranged in close proximity to each other,
    a sample rack for carrying samples and a reagent for converting catecholamines to their derivatives the sample rack being positioned in the rack mounting portion, and a suction and discharge nozzle moveable from the sample rack to the reaction vessel for transferring the samples and the reagent into the reaction vessel to form a reaction mixture therein and then to the sample injection port,
    transfer means including said suction and discharge nozzle for transferring the reaction mixture, which is positioned in said reaction vessel in a prescribed period of time to initiate a labeling reaction of derivatives of catecholamines in said reaction vessel, to a pre-column for capturing the labeled derivatives of catecholamines introduced through the sample injection port,
    a separating column for separating the labeled derivatives of catecholamines fed from the pre-column into components, and
    a fluorescence detector positioned downstream of the separation column.

13. A liquid chromatographic analyzer for analyzing a sample containing components for analysis by effecting the following steps of analysis:
    reacting the sample with a pre-labeling reagent to obtain a reaction mixture containing labeled components, concentrating the reaction mixture, and separating the labeled components from each other and detecting the separated labeled components by detectors;
    the steps of analysis being controlled to concurrently proceed by a control unit, thereby shortening the time for analysis per sample, said analyzer comprises:
    (a) container means for storing samples containing components for analysis and a pre-labeling reagent for the components at a constant temperature,
    (b) vessel means for reacting the sample with the pre-labeling reagent at a constant temperature to obtain a reaction mixture containing labeled components, said container means and said vessel means being arranged with a sample feeding section,
    (c) nozzle means for transferring one of the samples and the pre-labeling regent form said container means to said vessel means, said nozzle means moving from said container means to said vessel means to transfer said sample or said pre-labeling reagent, and for transferring said reaction mixture from said vessel means to a sample injection port,
    (d) means for concentrating the reaction mixture which is fed form said sample injection port and separating the labeled components from each other to provide separated labeled components,
    (e) means for detecting the separated labeled components, and
    (f) control unit means for controlling the steps of reacting the sample with a pre-labeling reagent to obtain a reaction mixture containing labeled components, concentrating the reaction mixture, and separating the labeled components from each other and detecting the separated labeled components by detectors concurrently, thereby shortening the time for analysis per sample.

* * * * *